United States Patent
Kojima et al.

(10) Patent No.: US 7,683,212 B2
(45) Date of Patent: Mar. 23, 2010

(54) METHODS FOR PRODUCING ACETIC ACID

(75) Inventors: Hidetaka Kojima, Himeji (JP); Hiroyuki Miura, Takasago (JP)

(73) Assignee: Daicel Chemical Industries, Ltd., Sakai-Shi (JP)

( * ) Notice: Subject to any disclaimer, the term of this patent is extended or adjusted under 35 U.S.C. 154(b) by 0 days.

(21) Appl. No.: 10/567,900

(22) PCT Filed: Dec. 19, 2005

(86) PCT No.: PCT/JP2005/023268

§ 371 (c)(1), (2), (4) Date: Feb. 10, 2006

(87) PCT Pub. No.: WO2006/070632

PCT Pub. Date: Jul. 6, 2006

(65) Prior Publication Data

US 2007/0093676 A1    Apr. 26, 2007

(30) Foreign Application Priority Data

Dec. 27, 2004    (JP)    ............... 2004-377223

(51) Int. Cl.
 *C07C 51/12*    (2006.01)
(52) U.S. Cl. ............... 562/519; 562/607; 562/608
(58) Field of Classification Search ................ 562/519
See application file for complete search history.

(56) References Cited

U.S. PATENT DOCUMENTS

| | | | | |
|---|---|---|---|---|
| 4,252,741 A * | 2/1981 | Porcelli et al. | ............... | 562/891 |
| 5,364,963 A * | 11/1994 | Minami et al. | ............... | 562/519 |
| 5,625,095 A * | 4/1997 | Miura et al. | ................ | 562/519 |
| 5,916,422 A * | 6/1999 | Kimura et al. | ............... | 203/16 |
| 5,939,585 A * | 8/1999 | Ditzel et al. | ................ | 562/519 |
| 6,066,762 A | 5/2000 | Yoneda et al. | | |
| 6,303,813 B1 * | 10/2001 | Scates et al. | ................ | 562/519 |
| 6,472,558 B1 * | 10/2002 | Key et al. | .................... | 562/519 |
| 6,573,403 B1 * | 6/2003 | Joensen | ...................... | 562/519 |
| 6,686,500 B1 * | 2/2004 | Watt | ........................... | 562/519 |
| 7,005,541 B2 * | 2/2006 | Cheung et al. | .............. | 562/519 |
| 7,098,363 B1 * | 8/2006 | Jones | ......................... | 562/519 |
| 7,223,886 B2 * | 5/2007 | Scates et al. | ................ | 562/608 |
| 2006/0281944 A1 * | 12/2006 | Hosono et al. | .............. | 562/519 |

FOREIGN PATENT DOCUMENTS

| | | | |
|---|---|---|---|
| EP | 687662 A2 * | 12/1995 | |
| JP | 47-3334 B | 1/1972 | |
| JP | 60-54334 A | 3/1985 | |
| JP | 60-239434 A | 11/1985 | |
| JP | 6-40999 A | 2/1994 | |
| JP | 8-5839 B2 | 1/1996 | |
| JP | 8-20555 A | 1/1996 | |
| JP | 3244385 B2 | 10/2001 | |
| JP | 2002-508759 A | 3/2002 | |
| JP | 2003-508363 A | 3/2003 | |
| JP | 2004-277297 A | 10/2004 | |
| WO | WO-02/062740 A1 | 8/2002 | |
| WO | WO-2004/060846 A1 | 7/2004 | |

OTHER PUBLICATIONS

Torrence, Paul, Celanese Ltd., Applied Homogeneous Catlysis with Organometallic Compounds (2nd Edition) (2002), vol. 1, p. 104-136.
Supplemental European Search Report for application No. 05 81 6451-A, issued Oct. 7, 2009.

* cited by examiner

*Primary Examiner*—Sikarl A Witherspoon
(74) *Attorney, Agent, or Firm*—Birch, Stewart, Kolasch & Birch, LLP (57) ABSTRACT

A method produces acetic acid by continuously reacting methanol with carbon monoxide in the presence of a rhodium catalyst, an iodide salt, methyl iodide, methyl acetate, and water; and thereby producing acetic acid at a production rate of 11 mol/L·hr or more while keeping the acetaldehyde content of a reaction mixture to 500 ppm or less, in which the reaction is carried out at a carbon monoxide partial pressure in a gaseous phase of a reactor of 1.05 MPa or more and/or at a methyl acetate content of the reaction mixture of 2 percent by weight or more to thereby keep the production rate of acetaldehyde to 1/1500 or less that of acetic acid. This method can reduce production of by-products without reducing the reaction rate of acetic acid even at a low water content and a low hydrogen partial pressure in a reaction system.

8 Claims, 1 Drawing Sheet

METHODS FOR PRODUCING ACETIC ACID

TECHNICAL FIELD

The present invention relates to methods for producing acetic acid by reacting methanol with carbon monoxide in the presence of a rhodium catalyst.

BACKGROUND ART

A method for producing acetic acid by continuously reacting methanol with carbon monoxide using a rhodium catalyst and methyl iodide in the presence of water is one of the most excellent industrial production methods of acetic acid (refer to Patent Document 1). The original method, however, requires a great deal of energy to remove water in a purification process, since the resulting reaction mixture has a high water content. If the water content of the reaction mixture is reduced, the rhodium catalyst is inactivated and the productivity of acetic acid decreases.

As a possible solution to reduce the water content of the reaction mixture without inactivating the rhodium catalyst, propose improved methods in which a catalyst stabilizer such as an iodide salt is added to the reaction system were proposed (refer to Patent Documents 2 and 3). The improvements in these methods serve to stabilize the rhodium catalyst and to reduce byproducts such as carbon dioxide and propionic acid. The methods, however, invite increase in by-produced carbonyl-containing reducing impurities to thereby decrease the quality of produced acetic acid. These impurities include acetaldehyde, as well as crotonaldehyde, 2-ethylcrotonaldehyde, and other products of consecutive reactions, such as aldol condensation, of acetaldehyde. In addition, the methods also invite increase in by-produced alkyl iodides, such as hexyl iodide derived from acetaldehyde. Such alkyl iodides will degrade palladium catalysts used in the production of vinyl acetate from acetic acid and ethylene.

Granted Japanese Patent No. 3244385 discloses a method for producing high-purity acetic acid by continuously reacting methanol with carbon monoxide in the presence of a rhodium catalyst, an iodide salt, and methyl iodide, in which the reaction is carried out while maintaining the acetaldehyde content of the reaction mixture to 400 ppm or less. This document mentions a specific method of maintaining the acetaldehyde content of the reaction mixture to 400 ppm or less by removing acetaldehyde from a process mixture circulating to a reactor, but it lacks a detailed description on inhibition of aldehyde production.

PCT Japanese Translation Patent Publication No. 2003-508363 discloses a technique for reducing impurities by controlling the hydrogen partial pressure within the range of 0.1 to 4 psia (0.7 to 27.6 kPa) at a low water content in a method for producing acetic acid by reacting methanol with carbon monoxide in the presence of a rhodium catalyst. Such an extremely low hydrogen partial pressure generally fails to ensure a sufficiently high catalytic activity in the production of acetic acid. Japanese Examined Patent Application Publication (JP-B) No. 8-5839 mentions that the production rate of acetic acid decreases at a low hydrogen partial pressure of 40 psi (276 kPa) or less. In addition, highly pure carbon monoxide containing a minimum amount of hydrogen is required for controlling the hydrogen partial pressure at such a very low level. The production of highly pure carbon monoxide requires enhanced facilities for purification and invites increased cost. The present inventors have verified that the acetaldehyde content and amounts of other byproducts cannot be sufficiently reduced even by this method.

PCT International Publication Number WO 2004/60846 discloses a process for producing acetic acid in which acetic acid is produced at a production rate (STY) of 15 mol/L·hr or more at a water content of 2 percent by weight or less and a rhodium content of 1000 ppm or more. According to this document, a reaction for producing methane ($CH_3OH+H_2 \rightarrow CH_4+H_2O$) takes priority over a water gas shift reaction ($CO+H_2O \rightarrow CO_2+H_2$), and water forms and accumulates in the reaction system at a water content in the reaction system of 5 percent by weight or less. To avoid this, the method uses methyl acetate in the reaction system for chemically controlling the water content. The added methyl acetate comes in contact with water in the system and is hydrolyzed into acetic acid and methanol. The resulting methanol is used as a raw material for the production of acetic acid. The increased rhodium content in the system, however, increases not only the production rate of acetic acid but also that of by-produced acetaldehyde. Acetic acid and acetaldehyde increase proportionally with increase in rhodium content. Specifically, acetaldehyde increases substantially proportionally with increase in acetic acid. At a low water content, the rate of aqueous gas shift reaction decreases to thereby decrease the hydrogen partial pressure. At such a low hydrogen partial pressure, the rates of hydrogenation reactions of acetaldehyde (e.g., $CH_3CHO+H_2 \rightarrow CH_3CH_2OH$) decrease to thereby increase the acetaldehyde content of the reaction mixture and increase the rate of condensation reactions of acetaldehyde. Consequently, reducing substances such as crotonaldehyde and 2-ethylcrotonaldehyde as products consecutive reactions of acetaldehyde increase to thereby cause poor results in a potassium permanganate test of the product acetic acid. The present inventors have verified the above facts as a result of investigations. In contrast, at a somewhat high hydrogen partial pressure, e.g., at a hydrogen partial pressure of 11 to 14 psi (75.8 to 96.5 kPa) as described in PCT International Publication Number WO 2004/60846, water formed upon by-production of methane must be removed. This requires extra energy and an extra agent for removing water and thereby reduces the production efficiency. This also increases the by-production of formic acid that is a reducing substance and causes poor results in a potassium permanganate test.

Applied Homogeneous Catalysis with Organometallic Compounds (2nd Edition) (2002), Volume 1, 104-136 (Celanese) relates to techniques for synthesizing acetic acid at a low water content and mentions that the stability of a rhodium complex is increased by adding lithium iodide, that the carbonylation reaction rate markedly increases with an increasing methyl acetate content at low water contents, and that the carbonylation reaction rate is increased by the action of the iodide salt. This document, however, lacks the description about the control of acetaldehyde content. The present inventors have found that while the addition of lithium iodide for improving the stability of a rhodium complex increases the production rate of acetic acid, it further increases the production rate of acetaldehyde.

JP-A No. 6-40999 discloses a method for producing acetic acid, in which a reaction is carried out while keeping the water content to about 10 percent by weight or less and the methyl acetate content to 2 percent by weight or more, and the resulting reaction mixture is distilled. This document mentions that the by-production of propionic acid decreases with an increasing methyl acetate content, and the propionic acid content of the reaction mixture becomes less than 500 ppm at a methyl acetate content of 2 percent by weight. As is described above, however, the reaction rate of acetaldehyde hydrogenation decreases under a low hydrogen partial pressure at a low water content, the acetaldehyde content of the reaction mixture increases to thereby increase the reaction rate of acetaldehyde condensation, although the production level of propionic acid due to carbonylation of ethanol decreases. As a result, reaction products of acetaldehyde condensation increase to thereby impair the quality of acetic acid. To achieve a process for efficiently producing acetic acid which saves resources and energy, the by-production of both acetaldehyde and consecutive reaction products of acetaldehyde, such as condensation reaction products, propionic acid, and hexyl iodide, must be effectively inhibited.

PCT International Publication Number WO 2002/62740 discloses a low-energy process for producing acetic acid using two or less distillation columns, in which a product flow contains propionic acid impurities at low level, and the level of aldehyde impurities in the product flow is controlled through a technique selected from (i) maintaining the hydrogen partial pressure in the reactor to less than about 6 psia (41.3 kPa) at a total pressure of from about 15 to 40 atmospheres (1.5 to 4 MPa) in the reactor; or (ii) maintaining the methyl iodide content of the reaction mixture of less than about 5 weight percent; or (iii) removing aldehyde impurities. The reduction in hydrogen partial pressure, however, increases by-production of consecutive reaction products of acetaldehyde including acetaldehyde condensation reaction products to thereby impair the quality of acetic acid, as mentioned above. The reduction in methyl iodide content reduces the production rates of not only acetaldehyde but also acetic acid, as described in Example of this document (Table 3). Namely, it reduces the production efficiency of acetic acid and is industrially and economically undesirable.

Patent Document 1: Japanese Examined Patent Application Publication (JP-B) No. 47-3334)

Patent Document 2: Japanese Unexamined Patent Application Publication (JP-A) No. 60-54334

Patent Document 3: JP-A No. 60-239434

Patent Document 4: Granted Japanese Patent No. 3244385

Patent Document 5: PCT Japanese Translation Patent Publication No. 2003-508363

Patent Document 6: Japanese Examined Patent Application Publication (JP-B) No. 8-5839

Patent Document 7: PCT International Publication Number WO 2004/60846

Patent Document 8: JP-A No. 6-40999

Patent Document 9: PCT International Publication Number WO 2002/62740

Non-Patent Document 1: Applied Homogeneous Catalysis with Organometallic Compounds (2nd Edition) (2002), Volume 1, 104-136 (Celanese)

DISCLOSURE OF INVENTION

Problem to be Solved by the Invention

Accordingly, an object of the present invention is to provide a method for efficiently producing high-quality acetic acid, which method can reduce production of by-products without reducing the reaction rate of acetic acid even at a low water content and a low hydrogen partial even at a low water content and a low hydrogen partial pressure in a reaction system.

Another object of the present invention is to increase the productivity of acetic acid and to inhibit by-productions of acetaldehyde and consecutive reaction products of acetaldehyde to thereby provide a simple and efficient process for producing acetic acid.

Means for Solving Problem

After intensive investigations on methods for producing acetic acid by carbonylating methanol in the presence of a rhodium catalyst, the present inventors obtained the following findings. Specifically, the content of active Rh[I] complex decreases at a low water content and a low hydrogen partial pressure in the reaction system, and that the production rate of acetic acid significantly decreases at a hydrogen partial pressure of less than 4 psi (27.6 kPa). To achieve a hydrogen partial pressure of less than 4 psi (27.6 kPa), a high-purity carbon monoxide (CO) feedstock having a hydrogen content of less than 0.01 percent by mole is required. This increases cost for CO purification facilities and for CO production. An increasing rhodium content proportionally increases the production rates of not only acetic acid but also by-produced acetaldehyde. A more severe problem at a low hydrogen partial pressure is that, of consecutive reactions of acetaldehyde, the reaction rate of condensation of acetaldehyde increases and the production levels of reducing substances such as crotonaldehyde and 2-ethylcrotonaldehyde increase to cause poor results in the potassium permanganate test and to impair the quality of acetic acid. Acetaldehyde must be removed by chemical treatment and/or separation to keep satisfactory quality of the product acetic acid. At such a high hydrogen partial pressure that the production rate of methane is higher than that of carbon dioxide, water produced upon the by-production of methane must be removed. This requires extra energy and the addition of an agent for removing water to thereby reduce the production efficiency and increase the production cost of acetic acid. This also increases the by-production level of formic acid which is a reducing substance and causes poor results in the potassium permanganate test.

To provide an efficient production process of acetic acid which can save resources and energy, the by-production of acetaldehyde and consecutive reaction products thereof must be positively reduced. Such consecutive reaction products of acetaldehyde include propionic acid; hexyl iodide; condensation reaction products of acetaldehyde, such as crotonaldehyde; and consecutive reaction products of these condensation reaction products. For the positive reduction of consecutive reaction products of acetaldehyde, acetaldehyde can be chemically treated to thereby reduce its content. For better result, acetaldehyde is preferably removed out from the reaction system. A more preferred solution is to inhibit the formation of acetaldehyde during the reaction. However, the technique of reducing the acetaldehyde formation by reducing the methyl iodide content is industrially and economically undesirable, since the technique acts to reduce not only the production rate of acetaldehyde but also that of acetic acid to thereby impair the production efficiency of acetic acid.

Consequently, the present inventors made detailed analyses of the reaction rate in relation with the formations of acetic acid as a main reaction product, and acetaldehyde, hydrogen (and carbon dioxide), and methane as major byproducts. Resultantly, they found that, of factors involved in reactions [reaction temperature, CO partial pressure and hydrogen partial pressure in the gaseous phase of the reactor, methyl iodide content, methyl acetate content, water content, rhodium content, and lithium iodide content (iodide salt) of the reaction mixture], only the CO partial pressure in the gaseous phase of the reactor and the methyl acetate content of the reaction mixture serve to accelerate the main reaction while inhibiting side reactions, as shown in following Table 1. In Table 1, an increasing number of "+" means a greater contribution to the formation, and an increasing number of "−" means a greater action of inhibiting the formation.

[Table 1]

TABLE 1

|  | Acetic acid | Acetaldehyde | $H_2$ ($CO_2$) | Methane |
|---|---|---|---|---|
| Reaction temperature (activation energy) | ++ | +++ | + | +++ |
| CO partial pressure | ++ | -- | - | --- |
| Hydrogen partial pressure | + | ++ | (-) | ++ |
| Methyl iodide content | ++ | ++ | + | ++ |
| Methyl acetate content | ++ | -- | - | - |
| Water content | + | + | +++ | ++ |
| Rhodium content | +++ | +++ | +++ | +++ |
| Lithium iodide content | ++ | ++ | + | +++ |

The data in Table 1 will be described in more detail below. The increase in reaction temperature increases the production rate of acetic acid, but also increases the production rate of acetaldehyde at an increasing rate higher than that of acetic acid. The increase in hydrogen partial pressure somewhat increases the production rate of acetic acid, but increases the production rate of acetaldehyde at an increasing rate higher than that of acetic acid. The increase in methyl iodide content increases the production rate of acetic acid, but further increases the production rate of acetaldehyde at an increasing rate equal to or higher than that of acetic acid. The increase in water content somewhat increases the production rate of acetic acid, but further increases the production rate of acetaldehyde at an increasing rate substantially equal to that of acetic acid. The increase in rhodium content increases the production rate of acetic acid, but also increases the production rate of acetaldehyde at an increasing rate substantially equal to that of acetic acid. The rhodium content significantly affects the production rates of these products and must be carefully set. The increase in lithium iodide content increases the production rate of acetic acid, but further increases the production rate of acetaldehyde at an increasing rate equal to or higher than that of acetic acid. The increase in lithium iodide content stabilizes the rhodium complex catalyst and increases the production rate of acetic acid, but also increases side reactions. The lithium iodide content must therefore be carefully set. Only the CO partial pressure and the methyl acetate content serve to accelerate the main reaction while inhibiting side reactions. The present inventors also revealed that the production rate of acetic acid can be increased while inhibiting by-production of acetaldehyde, regardless of the hydrogen partial pressure, by increasing the CO partial pressure and/or the methyl acetate content. The fact that the production rate of acetaldehyde is reduced by increasing the CO partial pressure and/or the methyl acetate content has not yet been known and has been first revealed by the present invention.

By setting more preferred reaction conditions based on these relations, the productivity of acetic acid can be increased while inhibiting the formation of consecutive reaction products of acetaldehyde such as aldehydes, alcohols, alkyl iodides, carboxylic acids, and carboxylic acid esters; and further consecutive reaction products thereof, such as aldehydes, alcohols, alkyl iodides, carboxylic acids, and carboxylic acid esters. This saves facilities and energy for separation and purification of the impurities and enables the production of high-purity acetic acid at low cost. The present invention has been achieved based on these findings and considerations.

Specifically, the present invention provides a method for producing acetic acid, including the steps of continuously reacting methanol with carbon monoxide in the presence of a rhodium catalyst, an iodide salt, methyl iodide, methyl acetate, and water and thereby producing acetic acid at a production rate of 11 mol/L·hr or more while keeping the acetaldehyde content of acetaldehyde of a reaction mixture to 500 ppm or less, in which the reaction is carried out at a carbon monoxide partial pressure in a gaseous phase of a reactor of 1.05 MPa or more and/or at a methyl acetate content of the reaction mixture of 2 percent by weight or more to thereby keep the production rate of acetaldehyde to 1/1500 or less of the production rate of acetic acid.

In this production method, the hydrogen partial pressure in the gaseous phase of the reactor is preferably 100 kPa or less and more preferably 70 kPa or less. The reaction is preferably carried out at a hydrogen partial pressure in the gaseous phase of the reactor of 70 kPa or less and a methyl acetate content of the reaction mixture of 3.1 percent by weight or more. The water content of the reaction mixture is more preferably 3 percent by weight or less.

In a preferred embodiment of the production method, acetic acid can be produced at a production rate of 15 mol/L·hr or more. In another preferred embodiment, acetic acid can be produced while keeping the production rate of acetaldehyde to 1/2500 or less of the production rate of acetic acid.

The method of the present invention can further include a purification process which includes the steps of separating the reaction mixture into acetic acid and a process mixture containing residual components and recovering acetic acid, separating and removing carbonyl impurities from the process mixture, and recycling the residual process mixture to the reactor.

According to a preferred embodiment, the method can further include a purification process which includes the steps of (A) separating the reaction mixture into a volatile component and a low-volatile component by distillation, the volatile component containing acetic acid, water, methyl acetate, and methyl iodide, and the low-volatile component containing the rhodium catalyst and the iodide salt; (B) separating the volatile component into a high-boiling component and a low-boiling component by distillation, the high-boiling component containing acetic acid, and the low-boiling component containing water, methyl acetate, and methyl iodide; (C) recycling the low-volatile component to the reactor; (D) separating and removing carbonyl impurities from the low-boiling component obtained in Step (B) to yield residual components; (E) recycling the residual components obtained in Step (D) to the reactor; (F) separating acetic acid from the high-boiling component obtained in Step (B) by distillation; and (G) treating the acetic acid obtained in Step (F) with a silver- or mercury-exchanged cation exchange resin. Steps (B), (D), and (F) can be carried out by using a total of three or less distillation columns.

EFFECT OF THE INVENTION

According to the present invention, the formation of by-products can be reduced without reducing the reaction rate of acetic acid even at a low water content and a low hydrogen partial pressure of the reaction system. High-quality acetic acid can thereby be efficiently produced. Furthermore, acetic acid can be efficiently produced with a high productivity using simple processes and facilities while inhibiting the formation of acetaldehyde and consecutive reaction products thereof.

DESCRIPTION OF THE SYMBOL 1 carbon monoxide
2 fresh methanol
3 reactor
4 gaseous purging flow
5 liquid product (reaction mixture)
6 evaporator (flasher)
7 bottom flow
8 overhead
9 a low-boiling component-acetic acid separation/distillation column
10 distillate (overhead)
11 a step for removing carbonyl impurities
12 line (reactor recycling line)
13 high-boiling component
14 acetic acid-distillation column
15 crude acetic acid
16 low-boiling component
17 high-boiling components having a boiling point higher than that of acetic acid
18 treatment tank filled with a cation exchange resin
19 acetic acid (product)
20 carbonyl impurities
9' distillation column
10' distillate
13' high-boiling component

BEST MODE FOR CARRYING OUT THE INVENTION

According to the present invention, acetic acid is produced by continuously reacting methanol with carbon monoxide using a rhodium catalyst. The rhodium catalyst generally exists as a rhodium complex in a reaction mixture. The rhodium catalyst can therefore be any one, as long as it is a rhodium complex soluble in the reaction mixture under reaction conditions or it can form the rhodium complex. Specifically, rhodium iodine complexes such as $RhI_3$ and $[Rh(CO)_2I_2]^-$, and rhodium carbonyl complexes are preferably used. The amount of the rhodium catalyst in terms of content in the reaction mixture is, for example, about 200 to about 3000 ppm, preferably about 300 to about 1000 ppm, and more preferably about 400 to about 900 ppm. The rhodium catalyst used in the reaction is generally recycled and reused.

In the present invention, an iodide salt is used typically for stabilizing the rhodium catalyst at a low water content and accelerating a reaction for producing acetic acid. The iodide salt can be any one, as long as it can yield iodide ions in the reaction mixture. Examples thereof are alkali metal iodides such as LiI, NaI, KI, RbI, and CsI; alkaline earth metal iodides such as $BeI_2$, $MgI_2$, and $CaI_2$; and iodide salts of aluminum group metals, such as $BI_3$ and $AlI_3$. Apart from the metal iodide salts, the iodide salt also includes organic iodide salts. Examples of the organic iodide salts are quaternary phosphonium iodide salts containing methyl iodide adducts or hydrogen iodide adducts of phosphines such as tributylphosphine and triphenylphosphine; and quaternary ammonium iodide salts containing methyl iodide adducts or hydrogen iodide adducts of nitrogen-containing compounds such as tertiary amines, pyridines, imidazoles, and imides. Among these iodide salts, alkali metal iodide salts such as LiI are preferred. The amount of the iodide salt is, in terms of iodide ion in the reaction mixture, for example, about 0.07 to about 2.5 mol/L and preferably about 0.25 to about 1.5 mol/L and is, in terms of content of the reaction mixture, about 3 to about 40 percent by weight and preferably about 4.5 to about 30 percent by weight. The iodide salt used in the reaction is generally recycled and reused.

Methyl iodide is used herein as a catalyst accelerator. The methyl iodide content of the reaction mixture is, for example, about 5 to about 20 percent by weight and preferably about 11 to about 16 percent by weight. Methyl iodide used in the reaction is generally recycled and reused.

The water content of the reaction mixture is generally about 15 percent by weight or less (for example, about 0.1 to about 15 percent by weight), preferably about 10 percent by weight or less (for example, about 0.3 to about 10 percent by weight), more preferably about 5 percent by weight or less (for example, about 0.5 to about 5 percent by weight), and particularly preferably about 3 percent by weight or less (for example, about 0.7 to about 3 percent by weight). An excessively high water content may increase the energy load for separating water in a purification system and requires large purification facilities. At low water contents under conventional reaction conditions, the rate of a water gas shift reaction decreases, the hydrogen partial pressure decreases, and by-production of condensation reaction products of acetaldehyde increases to thereby impair the quality of acetic acid. According to the present invention, however, the quality of acetic acid can be satisfactorily maintained without reducing the productivity thereof by carrying out the reaction at a CO partial pressure of 1.05 MPa or more and/or at a methyl acetate content of the reaction mixture of 2 percent by weight or less; keeping the production rate of acetaldehyde to 1/1500 or less the production rate of acetic acid; and maintaining the acetaldehyde content of the reaction mixture to 500 ppm or less.

The methyl acetate content of the reaction mixture is about 2 percent by weight or more, preferably about 3.1 percent by weight or more, and more preferably about 3.5 percent by weight or more, except when the reaction is conducted at a CO partial pressure in the gaseous phase of the reactor of 1.05 MPa or more. In this case, the methyl acetate content can be, for example, about 1 to about 2 percent by weight but is preferably about 2 percent by weight or more. The upper limit of the methyl acetate content of the reaction mixture is, for example, about 30 percent by weight, preferably about 15 percent by weight, and more preferably about 10 percent by weight. Methyl acetate is formed as a result of the reaction of raw material methanol with acetic acid. The by-production of byproducts such as acetaldehyde, hydrogen, and methane can be inhibited while increasing the production rate of acetic acid, by keeping the methyl acetate content of the reaction mixture at a high level. As the methyl acetate, one used in the reaction and/or one formed in the reaction is generally recycled and reused.

The residual main component of the reaction mixture is acetic acid, target product, which also serves as a reaction solvent. A typical reaction temperature of carbonylation according to the present invention is about 150° C. to about 250° C., preferably about 180° C. to about 220° C., and more preferably about 182° C. to about 195° C.

The CO partial pressure in the gaseous phase of the reactor is about 1.05 MPa or more, preferably about 1.10 MPa or more, and more preferably about 1.15 MPa or more, except when the reaction is conducted at a methyl acetate content of the reaction mixture of 2 percent by weight or more. In this case, the CO partial pressure may be, for example, about 0.8 to about 1.05 MPa but is preferably about 1.05 MPa or more. The upper limit of the CO partial pressure is, for example, about 3 MPa and preferably about 2.5 MPa. An increased CO partial pressure in the gaseous phase of the reactor can increase the stability of the rhodium catalyst and inhibit by-production of byproducts such as acetaldehyde, hydrogen, and methane while increasing the production rate of acetic acid.

The hydrogen partial pressure in the gaseous phase of the reactor is generally about 200 kPa or less, preferably about 100 kPa or less, and more preferably about 70 kPa or less. A high hydrogen partial pressure accelerates a methane-producing reaction ($CH_3OH+H_2 \rightarrow CH_4+H_2O$), an acetaldehyde-producing reaction ($CH_3OH+CO+H_2+CH_3CHO+H_2O$), and a propionic acid-producing reaction ($CH_3CHO+H_2 \rightarrow CH_3CH_2OH$, $CH_3CH_2OH+HI \rightarrow CH_3CH_2I+H_2O$, $CH_3CH_2I+CO+H_2O \rightarrow CH_3CH_2COOH+HI$). These reactions can be inhibited by reducing the hydrogen partial pressure. Hydrogen is mainly formed by a water gas shift reaction ($CO+H_2O \rightarrow CO_2+H_2$). The hydrogen partial pressure can therefore be reduced by reducing the water content of the reaction mixture. As is described above, at a reduced hydrogen partial pressure under conventional reaction conditions, by-production of condensation reaction products of acetaldehyde increases to thereby impair the quality of product acetic acid. According to the present invention, however, the quality of acetic acid can be satisfactorily maintained without reducing the productivity thereof even at a low hydrogen partial pressure, by carrying out the reaction at a CO partial pressure of 1.05 MPa or more and/or at a methyl acetate content of the reaction mixture of 2 percent by weight or less; keeping the production rate of acetaldehyde to 1/1500 or less the production rate of acetic acid; and holding the acetaldehyde content of the reaction mixture to 500 ppm or less. The lower limit of the hydrogen partial pressure is, for example, about 5 kPa and generally about 10 kPa. The hydrogen is formed as a result of the aqueous gas shift reaction and, additionally, may be introduced into the system together with raw material carbon monoxide.

The total pressure of the reactor is constituted by the CO partial pressure and the hydrogen partial pressure, partial pressures of other by-produced gases (methane, carbon dioxide, and nitrogen), and vapor pressures of the components in the reaction mixture and is generally within the range of about 1.5 to about 5 MPa.

According to the present invention, acetic acid is produced at a high production rate of 11 mol/L·hr or more (preferably about 15 mol/L·hr or more) while keeping the production rate of acetaldehyde to 1/1500 or less the production rate of acetic acid. To produce acetic acid at a high production rate under general conventional reaction conditions, the reaction temperature must be elevated and the contents of the rhodium catalyst, iodide salt, and methyl iodide must be increased. These conditions, however, also increases by-production of acetaldehyde. According to the present invention, however, the ratio of the production rate of acetaldehyde to that of acetic acid can be reduced to 1/1500 or less by carrying out the reaction at a CO partial pressure of 1.05 MPa or more and/or at a methyl acetate content of the reaction mixture of 2 percent by weight or less. The ratio of the production rate of acetaldehyde to that of acetic acid is preferably about 1/1800 or less, more preferably about 1/2000 or less, and particularly preferably about 1/2500 or less.

The reaction according to the present invention is carried out while keeping the acetaldehyde content of the reaction mixture to 500 ppm or less. By keeping the acetaldehyde content of the reaction mixture to 500 ppm or less, by-production of byproducts derived from acetaldehyde can be significantly inhibited. Examples of such byproducts are reducing substances such as crotonaldehyde and 2-ethylcrotonaldehyde; alkyl iodides such as hexyl iodide; and carboxylic acids such as propionic acid. The reaction according to the present invention is carried out at a CO partial pressure of 1.05 MPa and/or more or at a methyl acetate content of the reaction mixture of 2 percent by weight or less. Thus, the production rate of acetaldehyde can be markedly reduced. Accordingly, residual low-boiling components including water, methyl acetate, methyl iodide, and acetaldehyde after recovering acetic acid from the reaction mixture can be recycled to the reactor as intact. It is preferred, however, to separate and remove at least part of acetaldehyde from the low-boiling components and to recycle the residual components to the reactor, in order to minimize the acetaldehyde content of the reaction mixture. The acetaldehyde content of the reaction mixture is preferably about 450 ppm or less and more preferably about 400 ppm or less.

The reaction mixture is subjected to a purification process to thereby separate and recover acetic acid. For reducing the material cost, the rhodium catalyst, the iodide salt, methyl iodide, methyl acetate, and water are generally recycled to the reactor. By-produced carbonyl impurities such as acetaldehyde are preferably removed from a process mixture circulating into the reactor so as to inhibit by-production of various byproducts as a result of consecutive reactions of the carbonyl impurities. Among the carbonyl impurities, acetaldehyde is particularly preferably removed from the process mixture. The acetic acid is preferably brought into contact with a cation exchange resin with at least 1% of its active sites is replaced by a silver-based substance or a mercury-based substance to thereby reliably remove alkyl iodides such as hexyl iodide. The acetic acid after this treatment does not poison metal catalysts and is suitable typically as a raw material for acetic acid derivatives, such as vinyl acetate, which are produced using metal catalysts.

The purification process can comprise, for example, Step (A) for separating the reaction mixture into a volatile component and a low-volatile component by distillation, the volatile component comprising acetic acid, water, methyl acetate, and methyl iodide, and the low-volatile component comprising the rhodium catalyst and the iodide salt; Step (B) for separating the volatile component into a high-boiling component and a low-boiling component by distillation, the high-boiling component comprising acetic acid, and the low-boiling component comprising water, methyl acetate and methyl iodide; Step (C) for recycling the low-volatile component to the reactor; Step (D) for separating and removing carbonyl impurities from the low-boiling component obtained by Step (B) to yield a residual component; Step (E) for recycling the residual component obtained by Step (D) to the reactor; Step (F) for separating acetic acid from the high-boiling component obtained in Step (B) by distillation; and Step (G) for treating the acetic acid obtained in Step (F) with a silver- or mercury-exchanged cation exchange resin.

Figure 1:
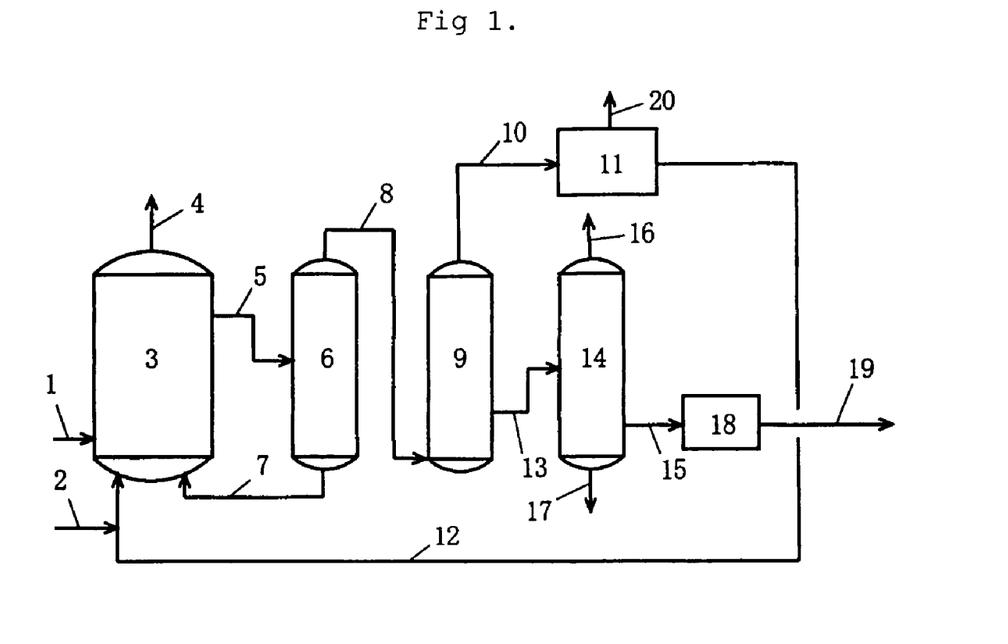
[FIG. 1] A production flow chart as an embodiment of the present invention.

FIG. 1 is a production flow chart showing an embodiment of the production method according to the present invention. In this embodiment, carbon monoxide 1, methanol 2, and, according to necessity, water are continuously fed to a carbonylation reactor 3. The liquid content in the reactor 3 is automatically kept to a predetermined level. The carbon monoxide 1 is preferably introduced to just below a stiffer equipped in the reactor 3. A gaseous purging flow 4 is exhausted from the reactor 3 to thereby prevent the accumulation of gaseous byproducts and maintain a set carbon monoxide partial pressure at a constant total pressure of the reactor. The reactor temperature is automatically controlled. A liquid product (reaction mixture) 5 is extracted from the reactor 3 at such a sufficient rate as to maintain the constant liquid level, introduced into the middle portion between the top and the bottom of an evaporator (flasher) 6, and subjected to evaporation [Step (A)]. In the evaporator 6, a catalyst mixture is extracted as a bottom flow 7 and returned to the reactor 3 [Step (C)]. The bottom flow 7 mainly comprises acetic acid containing the rhodium catalyst and the iodide salt together with small amounts of methyl acetate, methyl iodide, and water. An overhead 8 of the evaporator 6 mainly comprises product acetic acid and further comprises methyl iodide, methyl acetate, and water. The overhead 8 is introduced to the bottom, the vicinity of the bottom, or the side of a low-boiling component-acetic acid separation/distillation column (low-boiling component-acetic acid splitter column) 9 and subjected to distillation [Step (B)]. A distillate (overhead) 10 of the low-boiling component-acetic acid separation/distillation column 9 mainly comprises methyl iodide and methyl acetate with small amounts of water and acetic acid. The distillate 10 is subjected to a step 11 for removing carbonyl impurities [Step (D)] and returned via a line (reactor recycling line) 12 to the reactor 3 [Step (E)]. A high-boiling component 13 is extracted from the side in the vicinity of the bottom (or from the bottom) of the low-boiling component-acetic acid separation/distillation column 9 and is introduced into an acetic acid-distillation column 14 at the side thereof and subjected to distillation. Then, crude acetic acid 15 is extracted from the bottom or from the side in the vicinity of the bottom of the acetic acid-distillation column 14 [Step (F)]. A low-boiling component 16 including water is discharged out from the top of the acetic acid-distillation column 14, and high-boiling components 17 having a boiling point higher than that of acetic acid are discharged out from the bottom thereof. The low-boiling component 16 is recycled to the reactor 3. It is also possible to arrange a distillation column for distilling off water before the acetic acid-distillation column 14 and to feed the bottom flow of this column to the acetic acid-distillation column 14. The crude acetic acid 15 is further fed to a treatment tank 18 packed with a silver- or mercury-exchanged cation exchange resin [Step (G)]. In this step, alkyl iodides, such as hexyl iodide, contained in acetic acid in trace amounts are efficiently separated and removed to thereby yield high-quality acetic acid (product) 19.

In the carbonyl impurities removing step 11, acetaldehyde and other carbonyl impurities 20, such as acetaldehyde, crotonaldehyde, and butyraldehyde, are removed from the distillate (or overhead) 10 of the low-boiling component-acetic acid separation/distillation column 9. The carbonyl impurities can be removed, for example, by the method described in Granted Japanese Patent No. 3244385. For example, the carbonyl impurities can be removed by subjecting the distillate 10 of the low-boiling component-acetic acid separation/distillation column 9, the upper layer and/or the lower layer of the distillate 10, if separated, or a concentrate of these carbonyl impurities (hereinafter these are simply referred to as "process mixture") to distillation, extraction, or a combination of these such as extraction-distillation. Part or all of the residual components after removal of the carbonyl impurities contain useful components such as methyl iodide and methyl acetate and are returned via the line 12 to the reactor 3.

Specific examples of processes for separating the carbonyl impurities including acetaldehyde are a process of separating a process mixture containing acetaldehyde by distillation using one distillation column; a process of separating low-boiling components comprising acetaldehyde and methyl iodide from the other components by distillation and separating methyl iodide from acetaldehyde by distillation; and a process of separating methyl iodide from acetaldehyde by water extraction. This process utilizes the fact that acetaldehyde is highly miscible with water but methyl iodide is immiscible with water.

The amount of aldehydes to be removed in the carbonyl impurities removing step 11 is such an amount as to keep the acetaldehyde content of the reaction mixture during steady continuous reaction to 500 ppm or less, preferably about 450 ppm or less, and more preferably about 400 ppm or less.

Figure 2:
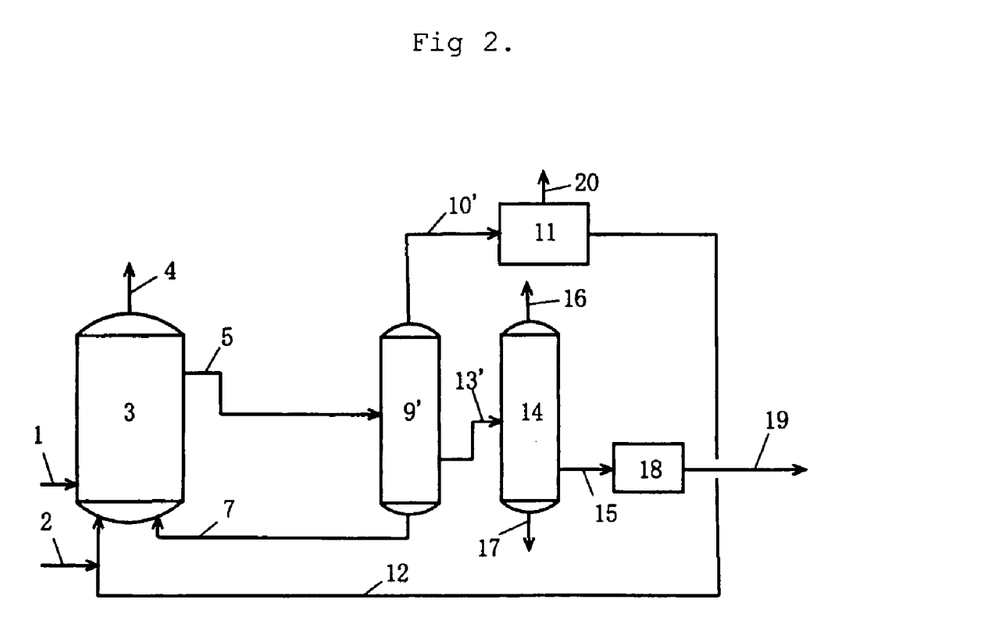
[FIG. 2] A production flow chart as another embodiment of the present invention.

FIG. 2 is a production flow chart showing another embodiment of the production method according to the present invention. In this embodiment, a liquid product (reaction mixture) 5 from a reactor 3 is introduced to the side of a distillation column 9' and subjected to distillation [Step (A) and Step (B)]. A distillate (overhead) 10' of the distillation column 9' mainly comprises methyl iodide, methyl acetate, and water with a small amount of acetic acid, is subjected to a carbonyl impurities removing step 11 [Step (D)] and returned via a line 12 to the reactor 3 [Step (E)]. The carbonyl impurities removing step 11 is conducted in the same manner as in FIG. 1. A catalyst mixture mainly comprising acetic acid containing rhodium catalyst and the iodide salt with small amounts of methyl acetate, methyl iodide, and water is extracted as a bottom flow 7 from the bottom of the distillation column 9' and is returned to the reactor 3 [Step (C)]. A high-boiling component 13' extracted from the side of the distillation column 9' is introduced into an acetic acid-distillation column 14 at the side thereof and is subjected to distillation. A crude acetic acid 15 is extracted from the side in the vicinity of the bottom of the acetic acid-distillation column 14 [Step (F)]. Water and other low-boiling components 16 are discharged out from the top of the acetic acid-distillation column 14, and high-boiling components 17 having a boiling point higher than that of acetic acid are discharged out from the bottom thereof. The low-boiling components 16 are recycled to the reactor 3. The crude acetic acid 15 is further fed to a treatment tank 18 packed with a silver- or mercury-exchanged cation exchange resin [Step (G)]. Thus, alkyl iodides such as hexyl iodide contained in acetic acid in trace amounts are efficiently separated and removed to thereby yield high-quality acetic acid 19.

The cation exchange resin treatment using a silver- or mercury-exchanged cation exchange resin can be conducted according to a known procedure, such as the method described in JP-B No. 5-21031, JP-A No. 4-282339, JP-A No. 5-301839, JP-B No. 7-14488, or JP-A No. 9-291059. Particularly, as described in JP-A No. 9-291059, a cation exchange resin in which at least 1% of its active sites is replaced with silver-based or mercury-based substance is preferably used, and the temperature is preferably elevated stepwise when the crude acetic acid 15 is brought in contact with the cation exchange resin. In this method, the flow rate of crude acetic acid 15 is preferably about 0.5 to about 40 bed volume per hour, and the treatment temperature is preferably within the range of about 17° C. to about 120° C. Better results can be obtained by bringing the crude acetic acid into contact with the cation exchange resin at about 17° C. to about 35° C. in early stages of operation and thereafter elevating the temperature stepwise. Thus, the contents of alkyl iodides such as hexyl iodide in acetic acid can be reduced to 1 ppb by weight or less.

According to the production method of the present invention, the production levels of acetaldehyde and consecutive reaction products thereof during reaction are very low, and Steps (B), (D), and (F) can thereby be conducted using a total of three or less distillation columns. For example, Steps (A) and (B) can be conducted using one distillation column, as illustrated in FIG. 2. Step (D) may use one distillation column for recovering acetaldehyde. According to the present invention, high-quality acetic acid can be produced even using a total of three or less distillation columns.

EXAMPLES

The present invention will be illustrated in further detail with reference to several examples below which by no means limit the scope of the present invention. The following acetic acid productions were conducted according to the production flow of FIG. 1. In units of pressure, "G" indicates the gauge pressure, and "A" indicates the absolute pressure.

Example 1

To a reactor 3 were continuously fed reaction raw materials (methanol 2 and carbon monoxide 1), a rhodium catalyst mixture 7 (containing a rhodium catalyst, an iodide salt, and acetic acid), and low-boiling components 12 (containing methyl iodide, methyl acetate, and water). The rhodium catalyst mixture 7 and the low-boiling components 12 had been recycled from a purification system. A reaction was thus conducted at a reaction pressure of 3.0 MPaG, a carbon monoxide (CO) partial pressure of 1.3 MPaA, a hydrogen ($H_2$) partial pressure of 0.03 MPaA, a reaction temperature of 188° C., and, of the reaction mixture, a methyl acetate (MA) content of 5.5 percent by weight, a rhodium (Rh) content of 800 ppm by weight, and a lithium iodide (LiI) content of 9.6 percent by weight. The reaction mixture 5 was flashed using an evaporator 6, and a high-boiling component containing the catalytic component (rhodium catalyst mixture 7) was pressurized by a pump and recycled to the reactor 3. Flashed components 8 were fed to a low-boiling component-acetic acid separation/distillation column 9 and separated into low-boiling components 10 and high-boiling components 13. The high-boiling components 13 were fed to a distillation column 14, and a crude acetic acid 15 having a purity as acetic acid of 99.5 percent by weight or more was obtained as a side flow in the vicinity of the bottom of the distillation column 14. The low-boiling components 10 were subjected to extraction with water to thereby remove 50 percent by mole of aectaldehyde (AD) in the low-boiling components 10 out of the system, and the residual low-boiling components were recycled via a line 12 to the reactor 3. Low-boiling components 16 obtained from the top of the distillation column 14 were also recycled to the reactor 3. The reaction mixture had a water content or the reaction mixture of 1.2 percent by weight, a methyl iodide (MeI) content of 14.3 percent by weight, and an acetaldehyde content of 400 ppm by weight.

The production rate of acetic acid (AC STY) was 19.4 mol/L·hr, the production rate of acetaldehyde (AD-STY) was 4.3 mmol/L·hr, and the ratio of the production rate of acetaldehyde to that of acetic acid (AD/AC) was 1/4500. The crude acetic acid 15 had a propionic acid (PA) content of 75 ppm by weight, a crotonaldehyde (CrD) content of 0.2 ppm by weight, and a residence time in the potassium permanganate test (permanganate time) of 190 minutes.

The crude acetic acid 15 was fed to a packed tank 18 (33° C.) filled with a strongly acidic cation exchange resin having a giant web structure bearing silver at active sites (trade name "AMBERLYST 15", a product of Rohm and Haas Company) at a flow rate of 7.2 bed volume per hour to thereby be treated with the ion exchange resin. No hexyl iodide (HexI) was detected in the product acetic acid 19. The detection limit of hexyl iodide is 0.2 ppb by weight.

The above procedure was repeated, except for recycling the low-boiling component 10 via the line 12 to the reactor 3 without removing acetaldehyde therefrom. The resulting reaction mixture had an acetaldehyde content of 1050 ppm by weight, and the crude acetic acid had a propionic acid (PA) content of 180 ppm by weight, a crotonaldehyde (CrD) content of 1.6 ppm by weight, and a residence time in the potassium permanganate test (permanganate time) of 40 minutes.

Example 2

To a reactor 3 were continuously fed reaction raw materials (methanol 2 and carbon monoxide 1), a rhodium catalyst mixture 7 (containing a rhodium catalyst, an iodide salt, and acetic acid), and low-boiling components 12 (containing methyl iodide, methyl acetate, and water). The rhodium catalyst mixture 7 and the low-boiling components 12 had been recycled from a purification system. A reaction was thus conducted at a reaction pressure of 2.7 MPaG, a carbon monoxide partial pressure of 1.2 MPaA, a hydrogen partial pressure of 0.031 MPaA, a reaction temperature of 186° C., and, of the reaction mixture, a methyl acetate content of 5.5 percent by weight, a rhodium content of 650 ppm by weight, and a lithium iodide content of 9.9 percent by weight. The reaction mixture 5 was flashed using an evaporator 6, and a high-boiling component containing the catalytic component (rhodium catalyst mixture 7) was pressurized by a pump and recycled to the reactor 3. Flashed components 8 were fed to a low-boiling component-acetic acid separation/distillation column 9 and separated into low-boiling components 10 and high-boiling components 13. The high-boiling components 13 were fed to a distillation column 14, and a crude acetic acid 15 having a purity as acetic acid of 99.5 percent by weight or more was obtained as a side how in the vicinity of the bottom of the distillation column 14. The low-boiling components 10 were subjected to extraction with water to thereby remove 30 percent by mole of acetaldehyde (AD) in the low-boiling components 10 out of the system, and the residual low-boiling components were recycled via a line 12 to the reactor 3. Low-boiling components 16 obtained from the top of the distillation column 14 were also recycled to the reactor 3. The reaction mixture had a water content of 1.8 percent by weight, a methyl iodide content of 12.1 percent by weight, and an acetaldehyde content of 400 ppm by weight.

The production rate of acetic acid was 11.6 mol/L·hr, the production rate of acetaldehyde was 3.2 mmol/L·hr, and the ratio of the production rate of acetaldehyde to that of acetic acid was 1/3600. The crude acetic acid 15 had a propionic acid content of 75 ppm by weight, a crotonaldehyde content of 0.2 ppm by weight, a hexyl iodide (HexI) content of 28 ppb by weight, and a residence time in the potassium permanganate test of 190 minutes.

The crude acetic acid 15 was fed to a packed tank 18 (33° C.) filled with a strongly acidic cation exchange resin having a giant web structure bearing silver at active sites (trade name "AMBERLYST 15", a product of Rohm and Haas Company) at a flow rate of 7.2 bed volume per hour and treated with the ion exchange resin. No hexyl iodide was detected in the product acetic acid.

The above procedure was repeated, except for recycling the low-boiling component 10 via the line 12 to the reactor 3 without removing acetaldehyde therefrom. The resulting reaction mixture had an acetaldehyde content of 820 ppm by weight, and the crude acetic acid had a propionic acid (PA) content of 120 ppm by weight, a crotonaldehyde (CrD) content of 0.5 ppm by weight, and a residence time in the potassium permanganate test (permanganate time) of 160 minutes.

Example 3

To a reactor 3 were continuously fed reaction raw materials (methanol 2 and carbon monoxide 1), a rhodium catalyst mixture 7 (containing a rhodium catalyst, an iodide salt, and acetic acid), and low-boiling components 12 (containing methyl iodide, methyl acetate, and water). The rhodium catalyst mixture 7 and the low-boiling components 12 had been recycled from a purification system. A reaction was thus conducted at a reaction pressure of 3.5 MPaG, a carbon monoxide partial pressure of 1.8 MPaA, a hydrogen partial pressure of 0.03 MPaA, a reaction temperature of 188° C., and, of the reaction mixture, a methyl acetate content of 5.3 percent by weight, a rhodium content of 800 ppm by weight, and a lithium iodide content of 10.9 percent by weight. The reaction mixture 5 was flashed using an evaporator 6, and a high-boiling component containing the catalytic component (rhodium catalyst mixture 7) was pressurized by a pump and recycled to the reactor 3. Flashed components 8 were fed to a low-boiling component-acetic acid separation/distillation column 9 and separated into low-boiling components 10 and high-boiling components 13. The high-boiling components 13 were fed to a distillation column 14, and a crude acetic acid 15 having a purity as acetic acid of 99.5 percent by weight or more was obtained as a side flow in the vicinity of the bottom of the distillation column 14. The low-boiling components 10 were subjected to extraction with water to thereby remove 25 percent by mole of acetaldehyde in the low-boiling components 10 out of the system, and the residual low-boiling components were recycled via a line 12 to the reactor 3. Low-boiling components 16 obtained from the top of the distillation column 14 were also recycled to the reactor 3. The reaction mixture had a water content of 1.7 percent by weight, a methyl iodide content of 14 percent by weight, and an acetaldehyde content of 400 ppm by weight.

The production rate of acetic acid was 23.5 mol/L·hr, the production rate of acetaldehyde was 2.3 mmol/L·hr, and the ratio of the production rate of acetaldehyde to that of acetic acid was 1/10000. The crude acetic acid 15 had a propionic acid content of 65 ppm by weight, a crotonaldehyde content of 0.3 ppm by weight, and a residence time in the potassium permanganate test of 190 minutes.

The crude acetic acid 15 was fed to a packed tank 18 (33° C.) filled with a strongly acidic cation exchange resin having a giant web structure bearing silver at active sites (trade name "AMBERLYST 15", a product of Rohm and Haas Company) at a flow rate of 7.2 bed volume per hour and treated with the ion exchange resin. No hexyl iodide was detected in the product acetic acid.

The above procedure was repeated, except for recycling the low-boiling component 10 via the line 12 to the reactor 3 without removing acetaldehyde therefrom. The resulting reaction mixture had an acetaldehyde content of 710 ppm by weight, and the crude acetic acid had a propionic acid (PA) content of 115 ppm by weight, a crotonaldehyde (CrD) content of 1.4 ppm by weight, and a residence time in the potassium permanganate test (permanganate time) of 80 minutes.

Comparative Example 1

To a reactor 3 were continuously fed reaction raw materials (methanol 2 and carbon monoxide 1), a rhodium catalyst mixture 7 (containing a rhodium catalyst, an iodide salt, and acetic acid), and low-boiling components 12 (containing methyl iodide, methyl acetate, and water). The rhodium catalyst mixture 7 and the low-boiling components 12 had been recycled from a purification system. A reaction was conducted at a reaction pressure of 2.8 MPaG, a carbon monoxide partial pressure of 0.97 MPaA, a hydrogen partial pressure of 0.14 MPaA, a reaction temperature of 187° C., and, of the reaction mixture, a methyl acetate content of 1.6 percent by weight, a rhodium content of 650 ppm by weight and a lithium iodide content of 5.0 percent by weight. The reaction mixture 5 was flashed using an evaporator 6, and a high boiling component containing the catalytic component (rhodium catalyst mixture 7) was pressurized by a pump and recycled to the reactor 3. Flashed components 8 were fed to a low-boiling component-acetic acid separation/distillation column 9 and separated into low-boiling components 10 and high-boiling components 13. The high-boiling components 13 were fed to a distillation column 14, and a crude acetic acid 15 having a purity as acetic acid of 99.5 percent by weight or more was obtained as a side flow in the vicinity of the bottom of the distillation column 14. The low-boiling components 10 were subjected to extraction with water to thereby remove 66 percent by mole of acetaldehyde in the low-boiling components 10 out of the system, and the residual low-boiling components were recycled via a line 12 to the reactor 3. Low-boiling components 16 obtained from the top of the distillation column 14 were also recycled to the reactor 3. The reaction mixture had a water content of 8.0 percent by weight, a methyl iodide content of 13.0 percent by weight, and an acetaldehyde content of 300 ppm by weight.

The production rate of acetic acid was 11.7 mol/L·hr, the production rate of acetaldehyde was 10 mmol/L·hr, and the ratio of the production rate of acetaldehyde to that of acetic acid was 1/1200. The crude acetic acid 15 had a propionic acid content of 350 ppm by weight, a crotonaldehyde content of 1.0 ppm by weight, a hexyl iodide content of 30 ppb by weight, and a residence time in the potassium permanganate test of 140 minutes.

The above procedure was repeated, except for recycling the low-boiling component 10 via the line 12 to the reactor 3 without removing acetaldehyde therefrom. The resulting reaction mixture had an acetaldehyde content of 800 ppm by weight, and the crude acetic acid had a propionic acid (PA) content of 600 ppm by weight, a crotonaldehyde (CrD) content of 3.0 ppm by weight, a hexyl iodide content of 100 ppb by weight, and a residence time in the potassium permanganate test (permanganate time) of 30 minutes.

Comparative Example 2

To a reactor 3 were continuously fed reaction raw materials (methanol 2 and carbon monoxide 1), a rhodium catalyst mixture 7 (containing a rhodium catalyst, an iodide salt, and acetic acid), and low-boiling components 12 (containing methyl iodide, methyl acetate, and water). The rhodium catalyst mixture 7 and the low-boiling components 12 had been recycled from a purification system. A reaction was thus conducted at a reaction pressure of 2.8 MPaG, a carbon monoxide partial pressure of 1.0 MPaA, a hydrogen partial pressure of 0.175 MPaA, a reaction temperature of 188° C., and, of the reaction mixture, a methyl acetate content of 1.3 percent by weight, a rhodium content of 660 ppm by weight, and a lithium iodide content of 22.9 percent by weight. The reaction mixture 5 was flashed using an evaporator 6, and a high-boiling component containing the catalytic component (rhodium catalyst mixture 7) was pressurized by a pump and recycled to the reactor 3. Flashed components 8 were fed to a low-boiling component-acetic avid separation/distillation column 9 and separated into low-boiling components 10 and high-boiling components 13. The high-boiling components 13 were fed to a distillation column 14, and a crude acetic acid 15 having a purity as acetic acid of 99.5 percent by weight or more was obtained as a side flow in the vicinity of the bottom of the distillation column 14. The low-boiling components 10 were recycled as intact via a line 12 to the reactor 3 without removing acetaldehyde therefrom. Low-boiling components 16 as an overhead of the distillation column 14 were also recycled to the reactor 3. The reaction mixture had a water content of 4.0 percent by weight, a methyl iodide content of 14.5 percent by weight, and an aectaldehyde content of 980 ppm by weight.

The production rate of acetic acid was 25.5 mol/L·hr, the production rate of acetaldehyde was 35 mmol/L·hr, and the ratio of the production rate of acetaldehyde to that of acetic acid was 1/600. The crude acetic acid 15 had a propionic acid content of 1800 ppm by weight, a crotonaldehyde content of 4.9 ppm by weight, and a hexyl iodide content of 720 ppb by weight.

These results are shown in Table 2. In Table 2, "$CO_2$—STY" indicates the production rate of carbon dioxide in mmol/L·hr; "$CH_4$—STY" indicates the production rate of methane in mmol/L·hr; "AD content a" represents the acetaldehyde content of the reaction mixture when the low-boiling components 10 were recycled to the reactor 3 without removing acetaldehyde therefrom; "AD content b" represents the acetaldehyde content of the reaction mixture when a predetermined amount of acetaldehyde was removed from the low-boiling components 10 and the remainder was recycled to the reactor 3; "Crude acetic acid a" means a crude acetic acid when the low-boiling components 10 were recycled to the reactor 3 without removing acetaldehyde therefrom; and "Crude acetic acid b" means a crude acetic acid when a predetermined amount of acetaldehyde was removed from the low-boiling components 10 and the remainder was recycled to the reactor 3.

[Table 2]

TABLE 2

|  |  | Example | | | Comparative Example | |
|---|---|---|---|---|---|---|
|  |  | 1 | 2 | 3 | 1 | 2 |
| Reaction condition | Temperature (° C.) | 188 | 186 | 188 | 187 | 188 |
|  | Pressure (MPaG) | 3.0 | 2.7 | 3.5 | 2.8 | 2.8 |
|  | CO partial pressure (MPaA) | 1.3 | 1.2 | 1.8 | 0.97 | 1.0 |
|  | $H_2$ partial pressure (kPaA) | 30 | 31 | 30 | 140 | 175 |
|  | Water content (% by weight) | 1.2 | 1.8 | 1.7 | 8.0 | 4.0 |
|  | MeI content (% by weight) | 14.3 | 12.1 | 14 | 13.0 | 14.5 |
|  | Rh content (ppm by weight) | 800 | 650 | 800 | 650 | 660 |
|  | LiI content (% by weight) | 9.6 | 9.9 | 10.9 | 5.0 | 22.9 |
|  | MA content (% by weight) | 5.5 | 5.5 | 5.3 | 1.6 | 1.3 |
|  | AD content a (ppm by weight) | 1050 | 820 | 710 | 800 | 980 |
|  | AD content b (ppm by weight) | 400 | 400 | 400 | 300 | — |
| Reaction result | Acetic acid STY (mol/L · hr) | 19.4 | 11.6 | 23.5 | 11.7 | 25.2 |
|  | AD-STY (mmol/L · hr) | 4.3 | 3.2 | 2.3 | 10 | 35 |
|  | AC/AD ratio (ratio in production rate) | 4500 | 3600 | 10000 | 1200 | 600 |
|  | $CO_2$-STY (mmol/L · hr) | 18 | 13 | 18 | 120 | 20 |
|  | $CH_4$-STY (mmol/L · hr) | 20 | 8 | 16 | 11 | — |
| Crude acetic acid a | PA content (ppm by weight) | 180 | 120 | 115 | 600 | 1800 |
|  | CrD content (ppm by weight) | 1.6 | 0.5 | 1.4 | 3.0 | 4.9 |
|  | Chameleon value (min) | 40 | 160 | 80 | 30 | — |
|  | HexI (ppb weight) | — | — | — | 100 | 720 |
| Crude acetic acid b | AD removal percentage (% by mol) | 50 | 30 | 25 | 66 | — |
|  | PA content (ppm by weight) | 75 | 75 | 65 | 350 | — |
|  | CrD content (ppm by weight) | 0.2 | 0.2 | 0.3 | 1.0 | — |
|  | Chameleon value (min) | 190 | 190 | 190 | 140 | — |
|  | HexI (ppb by weight) *1 | — | 28 | — | 30 | — |
|  | HexI (ppb by weight) *2 | <50 | <50 | <50 | — | — |

HexI (ppb by weight) *1: Data analyzed by ECD-GC
HexI (ppb by weight) *2: Data analyzed by GC-MS When the low-boiling component is recycled to the reactor without removing acetaldehyde therefrom as shown in "Crude acetic acid a" in Table 2, Examples 1 to 3 show a very small ratio of the production rate of acetaldehyde to that of acetic acid of 1/1500 or less, thereby significantly inhibit the by-production of consecutive reaction products of acetaldehyde, and show marked reduction in propionic acid content and crotonaldehyde content in the "crude acetic acid a" of about ½ to ¹⁄₁₀ those in Comparative Examples 1 and 2. According to Examples 1 to 3, 25 to 50 percent by mole of acetaldehyde is removed from the low-boiling components, and the remainder is recycled to the reactor to keep the acetaldehyde content of the reaction mixture to 500 ppm or less. Thus, the propionic acid content and the crotonaldehyde content in the "crude acetic acid b" are very low, the formation of byproducts derived from these compounds are inhibited, and the permanganate time is high as shown in "crude acetic acid b" in Table 2. In contrast, in Comparative Example 1, the ratio of the production rate of acetaldehyde to that of acetic acid is as great as 1/1200, and the "crude acetic acid b" has a high propionic acid content, a high crotonaldehyde content, and a low permanganate time, although the acetaldehyde removal percentage is 66 percent by mole, higher than those of Examples 1 to 3.

INDUSTRIAL APPLICABILITY

A process of the present invention can reduce production of by-products without reducing the reaction rate of acetic acid even at a low water content and a low hydrogen partial pressure in a reaction system, and can efficiently produce high-quality acetic acid.

The invention claimed is:

1. A method for producing acetic acid while inhibiting by-production of acetaldehyde by increasing carbon monoxide partial pressure or methyl acetate content, comprising the steps of:
   continuously reacting methanol with carbon monoxide in the presence of a homogeneous rhodium catalyst, an iodide salt, methyl iodide, methyl acetate, and water;
   producing acetic acid at a production rate of 11 mol/L·hr or more;
   keeping the acetaldehyde content of a reaction mixture to 500 ppm or less; and
   keeping the production rate of acetaldehyde to 1/1500 or less of the production rate of acetic acid,
   wherein the reaction is carried out at a carbon monoxide partial pressure in a gaseous phase of a reactor of 1.05 MPa or more and at a methyl acetate content of the reaction mixture of 2 to 10 percent by weight and at water content of the reaction mixture of 3 percent by weight or less and at a hydrogen partial pressure in the gaseous phase of the reactor of 70 kPa or less.

2. The method according to claim 1, wherein the reaction is carried out at a hydrogen partial pressure in the gaseous phase of the reactor of 70 kPa or less and a methyl acetate content of the reaction mixture of 3.1 to 10 percent by weight.

3. The method according to claim 1, wherein acetic acid is produced at a production rate of 15 mol/L·hr or more.

4. The method according to claim 1, wherein the production rate of acetaldehyde is kept to 1/2500 or less of the production rate of acetic acid.

5. The method according to claim 1, further comprising a purification process which comprises the steps of:
   separating the reaction mixture into acetic acid and a process mixture comprising residual components and recovering acetic acid;
   separating and removing carbonyl impurities from the process mixture to give a residual process mixture; and
   recycling the residual process mixture to the reactor.

6. The method according to claim 1, further comprising a purification process which comprises the steps of:
   (A) separating the reaction mixture into a volatile component and a low-volatile component by distillation, the volatile component comprising acetic acid, water, methyl acetate, and methyl iodide, and the low-volatile component comprising the rhodium catalyst and the iodide salt;
   (B) separating the volatile component into a high-boiling component and a low-boiling component by distillation, the high-boiling component comprising acetic acid, and the low-boiling component comprising water, methyl acetate, and methyl iodide;
   (C) recycling the low-volatile component to the reactor;
   (D) separating and removing carbonyl impurities from the low-boiling component obtained in Step (B) to yield a residual component;
   (E) recycling the residual component obtained in Step (D) to the reactor;
   (F) separating acetic acid from the high-boiling component obtained in Step (B) by distillation; and
   (G) treating the acetic acid obtained in Step (F) with a silver- or mercury-exchanged cation exchange resin.

7. The method according to claim 6, wherein Steps (B), (D), and (F) are carried out using a total of three or less distillation columns.

8. A method for producing acetic acid while inhibiting by-production of acetaldehyde by increasing carbon monoxide partial pressure or methyl acetate content, comprising the steps of:
   continuously reacting methanol with carbon monoxide in the presence of a rhodium catalyst which is a rhodium complex soluble in the reaction mixture under reaction conditions or can form the rhodium complex, an iodide salt, methyl iodide, methyl acetate, and water;
   producing acetic acid at a production rate of 11 mol/L·hr or more;
   keeping the acetaldehyde content of a reaction mixture to 500 ppm or less; and
   keeping the production rate of acetaldehyde to 1/1500 or less of the production rate of acetic acid,
   wherein the reaction is carried out at a carbon monoxide partial pressure in a gaseous phase of a reactor of 1.05 MPa or more and at a methyl acetate content of the reaction mixture of 2 to 10 percent by weight and at water content of the reaction mixture of 3 percent by weight or less and at a hydrogen partial pressure in the gaseous phase of the reactor of 70 kPa or less.

* * * * *